(12) United States Patent
Zhang et al.

(10) Patent No.: US 10,132,715 B2
(45) Date of Patent: Nov. 20, 2018

(54) TAP-SCAN BRIDGE DAMAGE DETECTION SYSTEM

(71) Applicants: China Road & Bridge Corporation, Beijing (CN); Tsinghua University, Beijing (CN)

(72) Inventors: Jianchu Zhang, Beijing (CN); Zhihai Xiang, Beijing (CN); Hong Liu, Beijing (CN); Zhihuai Li, Beijing (CN); Qiuhai Lu, Beijing (CN); Yaoguo Sun, Beijing (CN); Yanhua Wang, Beijing (CN); Lianyou Li, Beijing (CN); Zhaopu Shen, Beijing (CN)

(73) Assignees: CHINA ROAD & BRIDGE CORPORATION, Beijing (CN); TSINGHUA UNIVERSITY, Beijing (CN)

( * ) Notice: Subject to any disclaimer, the term of this patent is extended or adjusted under 35 U.S.C. 154(b) by 528 days.

(21) Appl. No.: 14/758,234

(22) PCT Filed: Dec. 27, 2013

(86) PCT No.: PCT/CN2013/090702
§ 371 (c)(1),
(2) Date: Jun. 28, 2015

(87) PCT Pub. No.: WO2014/101832
PCT Pub. Date: Jul. 3, 2014

(65) Prior Publication Data
US 2015/0323413 A1   Nov. 12, 2015

(30) Foreign Application Priority Data
Dec. 28, 2012   (CN) .......................... 2012 1 0584811

(51) Int. Cl.
*G01M 5/00* (2006.01)
*G01M 7/08* (2006.01)
(Continued)

(52) U.S. Cl.
CPC ........ *G01M 5/0008* (2013.01); *G01M 5/0033* (2013.01); *G01M 5/0066* (2013.01);
(Continued)

(58) Field of Classification Search
CPC .................................................. G01M 5/0033
(Continued)

(56) References Cited

U.S. PATENT DOCUMENTS

2012/0059600 A1   3/2012   Xiang et al.

FOREIGN PATENT DOCUMENTS

CN   101561379 A   10/2009
CN   101923027 A   12/2010
(Continued)

OTHER PUBLICATIONS

Xiang, Zhihai et al., The tap-scan damage detection method for beam structure, Chinese Journal of Solid Mechanics, Oct. 2011, vol. 32:p. 225-228.
(Continued)

*Primary Examiner* — Calvin Lee
(74) *Attorney, Agent, or Firm* — Loeb & Loeb LLP (57) ABSTRACT

A tap-scan bridge damage detection system comprises: a mobile cart (1) capable of moving on a to-be-detected bridge; a tap subsystem (2) mounted on the mobile cart (1) and used for applying a tap load to the to-be-detected bridge; a signal acquisition subsystem (3) mounted on the mobile cart and used for acquiring a response signal transferred from the to-be-detected bridge to the mobile cart; and a signal processing apparatus (4) connected to the signal acquisition subsystem (3) and used for receiving and pro-
(Continued)

cessing a signal acquired by the signal acquisition subsystem (3), and outputting the bridge damage information processed result. The tap-scan bridge damage detection system can detect bridge damage in a simple, convenient, efficient and accurate manner.

14 Claims, 4 Drawing Sheets

(51) Int. Cl.
    *G01N 29/04*     (2006.01)
    *G01N 29/265*     (2006.01)
    *G01N 29/46*     (2006.01)

(52) U.S. Cl.
    CPC ............ *G01M 5/0075* (2013.01); *G01M 7/08* (2013.01); *G01N 29/045* (2013.01); *G01N 29/265* (2013.01); *G01N 29/46* (2013.01); *G01N 2291/0232* (2013.01)

(58) Field of Classification Search
    USPC .................. 438/52, 14; 257/254, 48; 702/16
    See application file for complete search history.

(56) References Cited

FOREIGN PATENT DOCUMENTS

| | | |
|---|---|---|
| JP | 2002340805 A | 11/2002 |
| JP | 2006-349628 A | 12/2006 |

OTHER PUBLICATIONS

Yuan Zhao et al., Multiple Damage Detection of Simply Supported Beam Bridges, Journal of Tsinghua University (Sci & Tech), 2002, vol. 42, No. 4: p. 434-438.

Y.B. Yang et al., Extracting Bridge Frequencies from the Dynamic Response of a Passing Vehicle, Journal of Sound and Vibration, Vo. 272, No. 3, p. 471-493, 2004.

TAP-SCAN BRIDGE DAMAGE DETECTION SYSTEM

CROSS-REFERENCE TO RELATED APPLICATIONS

The present invention is the national stage application of the PCT International Application, Serial No. PCT/CN2013/090702, filed on Dec. 27, 2013, which claims the priority to the Chinese patent application, serial number 201210584811.1, filed on Dec. 28, 2012, whose contents are incorporated by reference in their entirety herein.

FIELD OF THE INVENTION

Embodiments of the invention relates to a bridge damage detection system and, in particular, to a tap-scan bridge damage detection system.

BACKGROUND

With the progress of science and technology as well as increasing demands in traffic and transportation, the number of bridges for use on various roads and in rail transit has grown at great speed. These bridges in use are constantly subjected to erosive impacts from the environment, such as temperature changes, strong winds and rainfalls, plus repeated and long-term actions from vehicle loads and strikes, and parts of the bridges even suffer from natural disasters like floods, earthquakes and so on, so over years of use, different degrees of fatigue effects and aging phenomena commonly appear in the bridges. As bodies of the bridges accumulate a great deal of exterior damages, many of them have become "danger bridges" in a certain sense. Bridges of such kind, located worldwide, have had quite a few instances of collapse, which posed a great threat to the security of human lives and properties. Thus, it is significant to detect damages of bridge in real time and effectively.

From the perspectives of the implementation period and the detection accuracy, the bridge detection comprises mainly the two modes of periodic inspection and real-time inspection: for the periodic inspection, such as visual inspection with instruments, bridge dynamic or static load tests, etc., it yields high accuracy but runs at a long time interval, which is unfavorable to a timely discovery of bridge damage and requires also an interruption of the bridge traffic, thus is difficult to implement; for the real-time detection, such as some bridge health monitoring systems, it does well in real-time function but yields low accuracy and runs with a high cost, thus it is difficult for it to gain wide use in short time.

From the perspective of real operation, existing bridge damage identification techniques may be divided into two modes: off-line local detection and on-line overall monitoring. The off-line local detection refers to probing carefully the damage(s) in structure using nondestructive detection means such as the observation by naked human eyes, ultrasound waves, electromagnetic eddy current and X-rays, etc., when the bridge is not in operation. Such methods yield higher accuracy of detection, but require always an interruption of the traffic, thus affecting the normal service of the bridge, need to know an approximate position of the damage in advance, and suffer from dead corners and low efficiency of detection. With the pre-installed sensor network, the on-line monitoring acquires bridge response signals in real time so as to infer the status of the damage(s). While such methods would not require an interruption of the bridge traffic, the detection accuracy is low, and there further exist issues such as installation of the sensor, transmission and storage of massive signals, and anti-noise capability and durability of the sensor.

SUMMARY OF THE INVENTION

In view of the above, there is an urgent need for developing a simple, convenient, efficient and accurate bridge damage detection solution. The inventors propose the technical solution of a tap-scan bridge damage detection system of embodiments of the invention based on their technical experience for years of practice in the relevant art and extensive expertise, and on constant research, development and improvement, further with verification by a lot of practice.

It is an object of embodiments of the invention to provide a tap-scan bridge damage detection system, which is capable of detecting bridge damage in a simple, convenient, efficient and accurate manner.

To achieve the above object, embodiments of the invention provide a tap-scan bridge damage detection system, comprising: a mobile cart capable of moving on a to-be-detected bridge; a tap subsystem mounted on the mobile cart and used for applying a tap load to the to-be-detected bridge; a signal acquisition subsystem mounted on the mobile cart and used for acquiring a response signal transferred from the to-be-detected bridge to the mobile cart; and a signal processing apparatus connected to the signal acquisition subsystem and used for receiving and processing the signal acquired by the signal acquisition subsystem, and outputting the processed result of bridge damage information.

Preferably, in the above tap-scan bridge damage detection system, a driving apparatus is further comprised, the mobile cart being connected to the driving apparatus and driven by the driving apparatus to move on the to-be-detected bridge.

Preferably, in the above tap-scan bridge damage detection system, the mobile cart comprises: a cart body; and wheels mounted on the cart body, the wheels being rigid wheel disks and being in direct contact with the surface of the to-be-detected bridge.

Preferably, in the above tap-scan bridge damage detection system, the wheels comprise a front wheel and two rear wheels, the front wheel being located on a longitudinal axis of the cart body of the mobile cart, and the two rear wheels being mounted symmetrically at two sides of the longitudinal axis of the cart body.

Preferably, in the above tap-scan bridge damage detection system, the tap subsystem comprises: a tap apparatus mounted on the mobile cart and used for generating a tap load and applying the tap load to the to-be-detected bridge; and a tap controlling apparatus connected to the tap apparatus and used for controlling the tap apparatus to generate a predetermined tap load.

Preferably, in the above tap-scan bridge damage detection system, the tap apparatus is a vibration shaker, and the vibration shaker is mounted on the cart body of the mobile cart, wherein a vibration excitation force produced by the vibration shaker acts upon the cart body of the mobile cart, and then the tap load is transferred to the to-be-detected bridge via the mobile cart.

Preferably, in the above tap-scan bridge damage detection system, the signal acquisition subsystem comprises one or more signal pickup apparatuses, the signal pickup apparatus being mounted on the mobile cart and used for acquiring a response signal transferred from the to-be-detected bridge to the mobile cart.

Preferably, in the above tap-scan bridge damage detection system, the signal pickup apparatus is an acceleration sensor.

Preferably, in the above tap-scan bridge damage detection system, the acceleration sensor is one in number and is installed on a through-shaft of the two rear wheels of the mobile cart.

Preferably, in the above tap-scan bridge damage detection system, the acceleration sensor is located at the center of the through-shaft, and the tap apparatus is located directly above the acceleration sensor.

Preferably, in the above tap-scan bridge damage detection system, the signal processing apparatus comprises: a spectrum obtaining apparatus connected to the signal pickup apparatus and used for transforming the signal detected by the signal pickup apparatus to obtain a signal spectrum at each position of the bridge surface; a spectrum envelope extracting apparatus used for extracting from the signal spectrum a spectrum envelope corresponding to a frequency band of the tap force of the tap apparatus; a damage index calculating apparatus for calculating a damage index at each position of the surface of the to-be-detected bridge according to the extracted spectrum envelope; and a damage position determining apparatus for determining a position of damage in the structure based on the damage index at each position of the surface of the to-be-detected bridge.

The tap-scan bridge damage detection system of embodiments of the invention has at least the following advantages and characteristics:

The tap-scan bridge damage detection system of embodiments of the invention has a strict theoretical basis. Detection signals may be obtained by scanning the to-be-detected bridge without requiring traffic blocking. The damage information of the bridge may be obtained directly from the detection signals without requiring the a priori damage information of the bridge. Thus, the operation is simple and easy to implement with high efficiency. By means of the tap-scan bridge damage detection system of embodiments of the invention, the damage status of a bridge may be readily learnt with convenience, so that potential risks at the bridge may be discovered in time, thus avoiding the occurrence of bridge accidents.

The tap-scan bridge damage detection system of embodiments of the invention is high in sensitivity, in which the detection requires shorter time without special detection conditions and yields high accuracy at a low cost, and as compared to the aforementioned existing bridge detection modes, it incorporates the advantages of various existing detection modes while avoiding their shortcomings.

The tap-scan bridge damage detection system of embodiments of the invention has a high anti-interference capability, for which an accurate detection result may be obtained without the necessity to interrupt the bridge traffic during the detection of a bridge, where the implementation is strongly operable without affecting the normal traffic and transportation functions of the bridge.

The tap-scan bridge damage detection system of embodiments of the invention enables the convenient and immediate implementation of detection without necessarily knowing in advance information on the complete characteristics of bridge structure prior to the detection of the bridge.

The tap-scan bridge damage detection system of embodiments of the invention is simple in structure and costs less manual labor during detection, and it is adaptable to various detection environments.

The above description is a summary of the technical solution of embodiments of the invention. In the following specific embodiments of the invention are enumerated in order to make the technical means clearer for implementation according to the contents of the description and make the above and other objects, features and advantages of embodiments of the invention more apparent and understandable.

BRIEF DESCRIPTION OF THE DRAWINGS

By reading through the detailed description of preferred embodiments as follows, the various other advantages and benefits will become apparent to the ordinarily skilled persons in the art. The drawings are merely used for illustration of the preferred embodiments and are not considered to be limitations to embodiments of the invention. Further, throughout the drawings, the same reference signs are used to denote the same parts. In the drawings.

DESCRIPTION OF REFERENCE SIGNS OF THE MAIN ELEMENTS

1 Mobile cart
10 Driving apparatus
11 Cart body
12 Front wheel
13 Rear wheel
14 Through-shaft
2 Tap subsystem
21 Tap apparatus
22 Tap controlling apparatus
3 Signal acquisition subsystem
31 Signal pickup apparatus
4 Signal processing apparatus
L Cart body axis

DETAILED DESCRIPTION OF THE INVENTION

Exemplary embodiments of the present disclosure are described hereinafter in more detail with reference to the drawings. Although the drawings display the exemplary embodiments of the present disclosure, it is to be understood that the present disclosure may be carried out in various forms and should not be confined to the herein elucidated embodiments. Instead, these embodiments are provided for a more thorough understanding of the disclosure and for enabling to convey the scope of the present disclosure more comprehensively to the persons skilled in the art.

Figure 1:
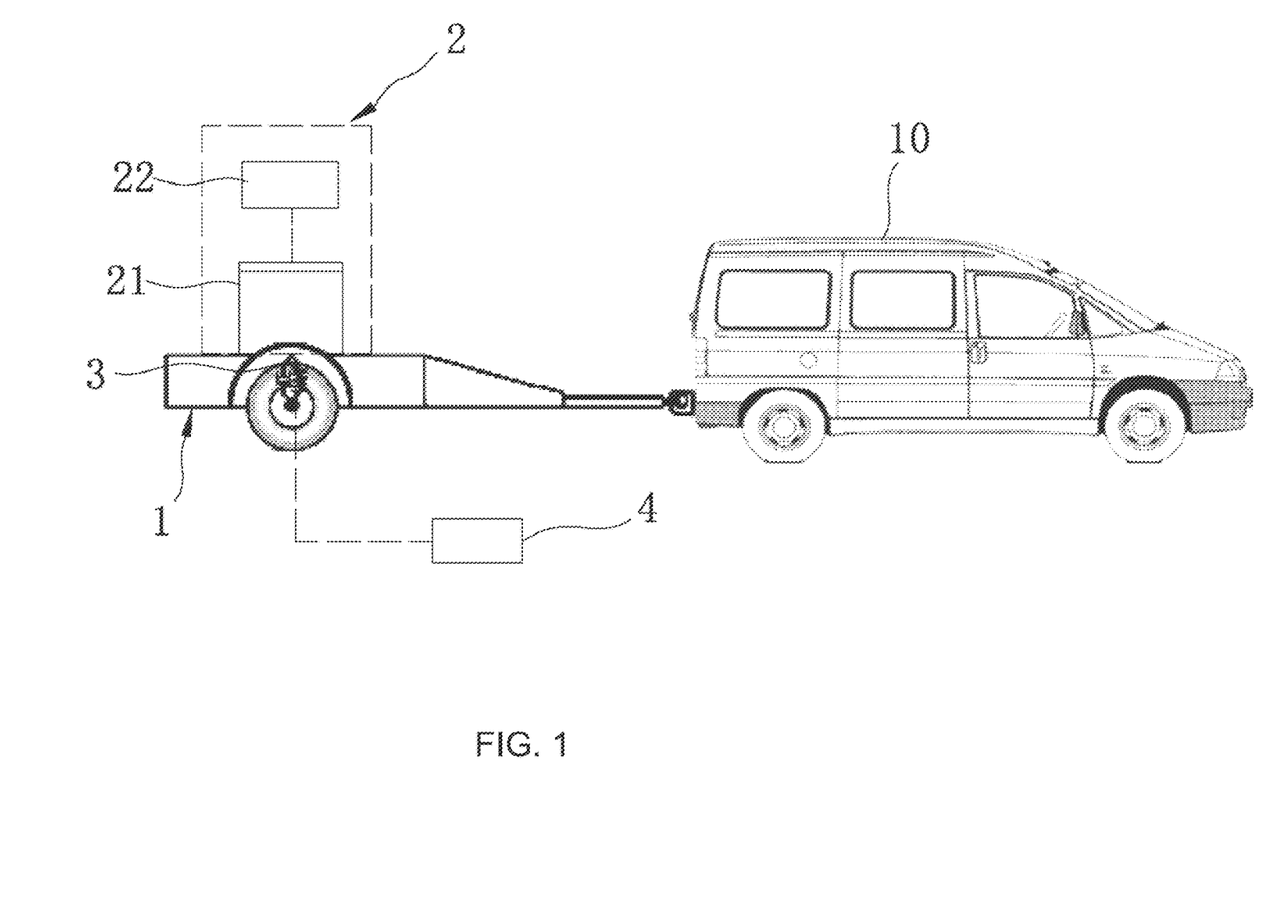
FIG. 1 is a composition schematic diagram of a tap-scan bridge damage detection system according to embodiments of the invention.

Please refer to FIG. 1, which is a composition schematic diagram of a tap-scan bridge damage detection system according to embodiments of the invention. As shown in FIG. 1, the tap-scan bridge damage detection system according to embodiments of the invention comprises mainly: a mobile cart 1 capable of moving on a to-be-detected bridge; a tap subsystem 2 mounted on the mobile cart 1 and capable of moving along with the mobile cart 1, the tap subsystem 2 being used mainly for applying a tap load to the to-be-detected bridge and being capable of causing the mobile cart 1 to apply the tap load to the to-be-detected bridge while moving on the to-be-detected bridge; a signal acquisition subsystem 3 mounted on the mobile cart 1 and used for acquiring a response signal of the tap load transferred from the to-be-detected bridge to the mobile cart 1; and a signal processing apparatus 4 connected to the signal acquisition subsystem 3, receiving and processing the signal acquired by the signal acquisition subsystem 3, and outputting the processed result reflecting bridge damage information.

The mobile cart 1 bears the tap subsystem 2, carrying it to move on the to-be-detected bridge. While the mobile cart 1 travels, the tap subsystem 2 may apply continuously a tap load to realize a tap-scan of the entire to-be-detected bridge. The mobile cart 1 may be connected to a driving apparatus 10 and driven by the driving apparatus 10 to move on the to-be-detected bridge. In the present embodiment, the driving apparatus 10 is a pulling vehicle that pulls the mobile cart 1 to move. In other embodiments, the mobile cart 1 may alternatively have power itself so as to move on the bridge. Additionally, in order to enable a convenient and accurate determination of the bridge damage position in later time, the driving apparatus 10 and the mobile cart 1 should be kept in uniform motion as far as possible.

Figure 2:
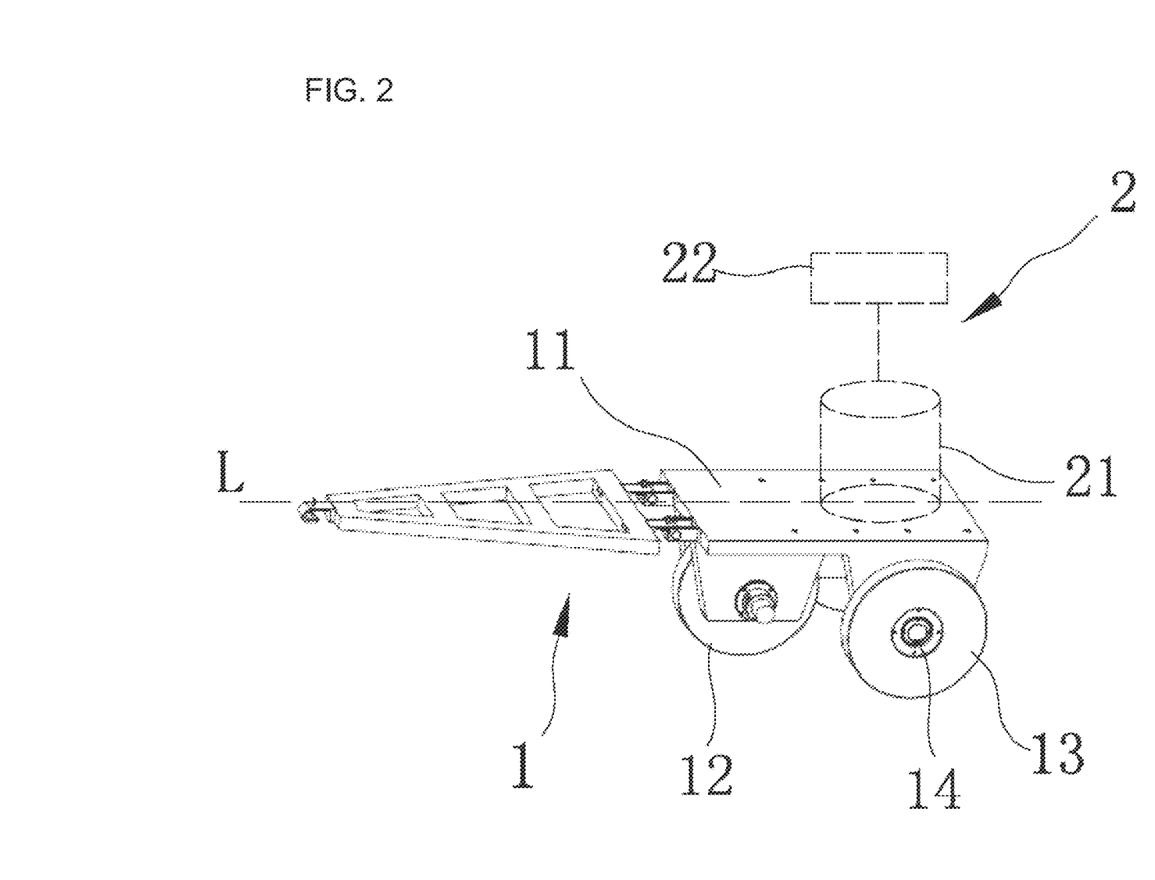
FIG. 2 is a structure schematic diagram of a tap subsystem mounted on a mobile cart in an embodiment of the tap-scan bridge damage detection system according to embodiments of the invention.

Please refer to FIG. 2, which is a structure schematic diagram of a tap subsystem mounted on a mobile cart in an embodiment of the tap-scan bridge damage detection system according to embodiments of the invention. As shown in FIG. 2, the tap subsystem 2 comprises a tap apparatus 21 and a tap controlling apparatus 22, wherein the tap apparatus 21 is mounted on the mobile cart 1 and the tap apparatus 21 is used for generating a tap load which is applied to the to-be-detected bridge. In the present embodiment, the tap apparatus 21 is a vibration shaker that is mounted on a cart body 11 of the mobile cart 1, where a vibration excitation force produced by the vibration shaker acts directly upon the cart body 11 of the mobile cart 1, and then the tap load is transferred, via the cart body, the wheels, etc. of the mobile cart, to the surface of the to-be-detected bridge. In other words, in addition to providing support, the mobile cart 1 is also responsible for transferring the tap load generated by the vibration shaker, and accordingly, the mobile cart per se should be specially designed to reduce or completely eliminate the buffering effect for the tap load, such that the tap load may be transferred integrally and effectively to the to-be-detected bridge. In the present embodiment, for example, the mobile cart 1 may be designed into a rigid body with each part of the cart body interconnected by rigid connection, while the wheels are mounted below the cart body or at two sides of the cart body, wherein the wheels are rigid wheel disks (such as a steel wheel disk), and an outer edge of the wheels is free of a buffer element such as a plastic tire, or in other words, an outer edge of the rigid wheel disks is in direct contact with the surface of the to-be-detected bridge. A suspension system of the cart is improved to avoid filtering of the tap load by means of the above structure, and further preferably, one front wheel 12 and two rear wheels 13 are arranged for the mobile cart, wherein the front wheel 12 is located on a longitudinal axis L of the cart body of the mobile cart and the two rear wheels 13 are located symmetrically at two sides of the axis L of the cart body, and the front wheel 12 and the two rear wheels 13 form an isosceles triangle such that the movement of the mobile cart 1 is more stable and that the cart can still travel stably forward without leaping or bumping when the cart body is subjected to the tap load.

The above-said vibration shaker is a conventional device and instances of many specifications are commercially available, of which the structures and functions will not be described here in detail.

The tap controlling apparatus 22 is connected to the tap apparatus 21 and is used for controlling the tap apparatus 21, e.g. a frequency of tap thereof, an amplitude of the tap force and so on, such that the tap apparatus can apply a tap load of a predetermined amplitude at a predetermined frequency band to the cart body of the mobile cart and to the to-be-detected bridge. In the present embodiment, the tap apparatus 21 is a vibration shaker and the tap controlling apparatus 22 is correspondingly a vibration shaker controller, of which the structures and principles are already conventional techniques and will not be described here in detail.

Figure 3:
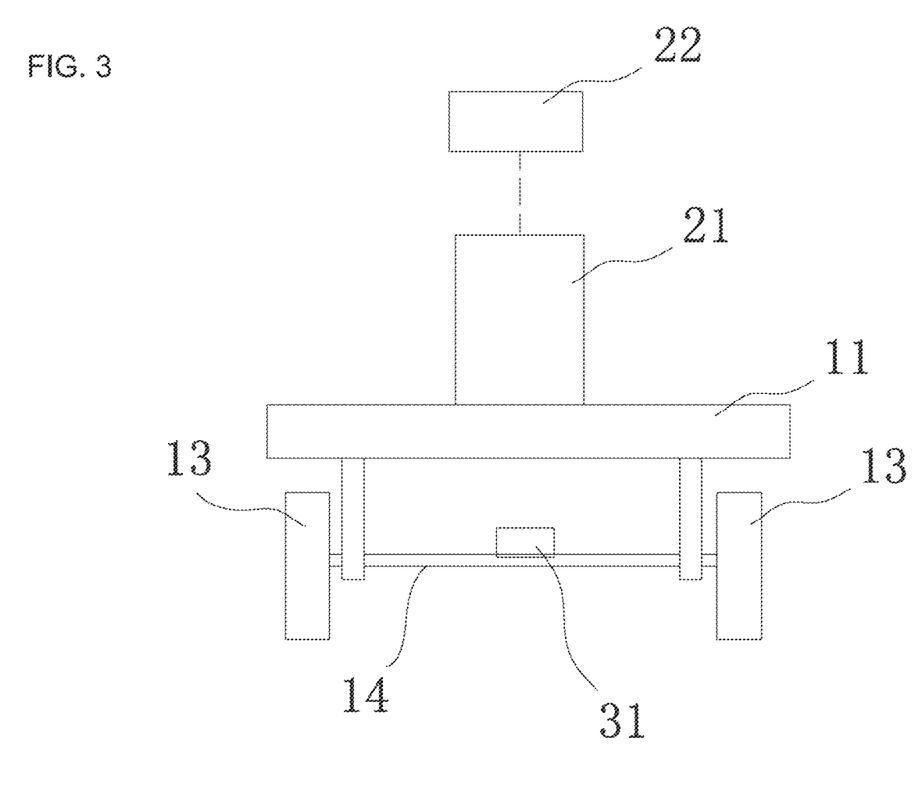
FIG. 3 is a structure schematic diagram of a signal detection apparatus mounted on a mobile cart in an embodiment of the tap-scan bridge damage detection system according to embodiments of the invention.

Please refer to FIG. 3, which is a structure schematic diagram of a signal acquisition subsystem mounted on a mobile cart in an embodiment of the tap-scan bridge damage detection system according to embodiments of the invention. As shown in FIG. 3, the signal acquisition subsystem is mounted on the mobile cart 1 and used for acquiring a response signal transferred from the to-be-detected bridge to the mobile cart 1, where the mobile cart 1 plays a role of transferring the bridge response signal and thus is further required to be preferably a rigid structure which has, as stated above, sufficient rigidity not to cut down on the transferring of the response signal, and such rigid structure of the mobile cart would cause no generation of an interference signal from itself, which would otherwise affect the signal acquisition of the signal acquisition subsystem 3.

The signal acquisition subsystem 3 may comprise one or more signal pickup apparatus 31 that may be directly mounted on the mobile cart 1 and is used for acquiring directly a response signal of the tap load transferred from the to-be-detected bridge to the mobile cart 1. The signal pickup apparatus 31 may be a sensor such as conventionally an acceleration sensor, a velocity sensor, or a displacement sensor, etc. In the present embodiment, the signal pickup apparatus 31 is an acceleration sensor and is one in number, and the acceleration sensor may be mounted at any position on the mobile cart 1. In order to enable maximum sensitivity and accuracy for the signal acquisition, it is preferred that the acceleration sensor is mounted on a through-shaft 14 of the two rear wheels 13 of the mobile cart 1, and the tap apparatus 21 (i.e. vibration shaker) is located directly above the acceleration sensor. Generally, the vibration shaker is directly mounted at the center of the cart body 11 of the mobile cart, while the acceleration sensor is located at the center of the through-shaft 14, at which position an optimal response signal of the tap load may be acquired.

Of course, the signal pickup apparatus 31 may be adapted flexibly in terms of the types used, the set number and the position(s), etc. according to the practical circumstances and requirements. A person skilled in the art may figure out various embodiments from the above disclosed ones by variations, but those embodiments should still belong to the scope of embodiments of the invention.

Figure 4:
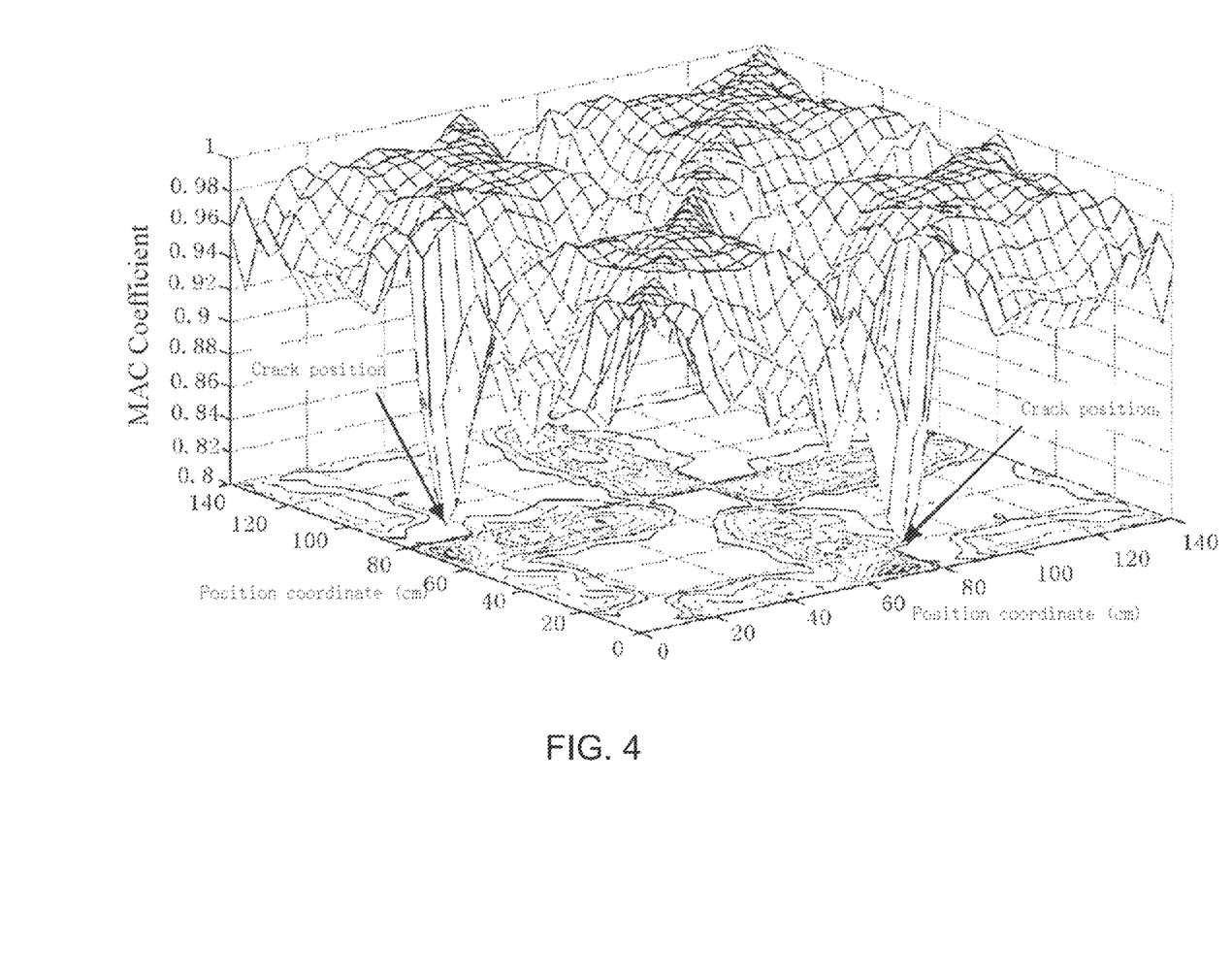
FIG. 4 is a spectrum schematic diagram of a detection signal in an embodiment of the tap-scan bridge damage detection system according to embodiments of the invention.

The signal processing apparatus 4 is connected to the signal acquisition subsystem 3, receiving and processing the response signal of the bridge tap load acquired by it, and outputting the processed result reflecting bridge damage information. The signal processing apparatus 4 may be a computer system. In a real application, the computer system may be connected to the sensor on the mobile cart via a conventional signal acquisition device to obtain the signal. In order to obtain detection data of high quality, a high-accuracy data acquisition card may be adopted, and in the case of a multi-channel data acquisition, a synchronization characteristic of each data acquisition channel must be further ensured. In the present embodiment, the signal pickup apparatus 31 is an acceleration sensor, and the acquired signal should be an acceleration spectrum of a tap response of the to-be-detected bridge where the mobile cart 1 travels past. Referring to FIG. 4, where a spectrum schematic diagram of a detection signal in an embodiment of the tap-scan bridge damage detection system according to embodiments of the invention is shown, the signal processing apparatus of the embodiment may correspondingly comprise: a spectrum obtaining apparatus, a spectrum envelope extracting apparatus, a damage index calculating apparatus and a damage position determining apparatus.

Therein, the spectrum obtaining apparatus is connected to the signal pickup apparatus 31, i.e. the acceleration sensor, for transforming a signal detected by the acceleration sensor to obtain an acceleration signal spectrum at each position of the bridge surface. Specifically, according to the detection accuracy requirement and the practical circumstances, the spectrum obtaining apparatus may divide the surface of the to-be-detected bridge into a plurality of small portions, and the mobile cart 1 carries the tap subsystem 2 and the signal acquisition subsystem 3 to scan each bridge surface portion necessarily for a period of time, during which the signals obtained by the sensor correspond to a sensor signal distribution over this period of time. Subsequently, the spectrum obtaining apparatus transforms the distribution of a series of sensor signals over time to obtain a corresponding representation of the signals in the frequency domain or scale domain. The transformation process may be implemented by a conventional transformation in the existing relevant art, e.g. a short time Fourier transformation or a wavelet transformation and so on. By means of the transformation, the spectrum obtaining apparatus may obtain a signal frequency spectrum or scale spectrum corresponding to each position of the bridge surface.

The spectrum envelope extracting apparatus extracts, from the signal spectrum obtained by the spectrum obtaining apparatus, a spectrum envelope that corresponds to a frequency band of the tap force from the tap apparatus.

The damage index calculating apparatus calculates a damage index at each position of the surface of the to-be-detected bridge according to the extracted spectrum envelope, the damage index reflecting a degree of similarity between the spectrum envelope at the position and the spectrum envelope at other positions. The damage index may be calculated in many ways. According to one embodiment of the invention, the damage index may be calculated as follows. Firstly, the extracted spectrum envelope is converted into a spectrum vector. This step of conversion may be performed by using the amplitudes at a plurality of frequencies in the obtained spectrum envelope as components of the spectrum vector. The number of the components of the spectrum vector may be determined depending on the accuracy of detection and the processing performance of the system, etc. The frequencies corresponding to the components may be distributed evenly or unevenly within the frequency band of the spectrum envelope. However, for the to-be-detected bridge, the way of selecting frequency band at each position should be the same; thereafter, the damage index may be obtained by using the MAC coefficient, where a formula for calculating an MAC coefficient matrix is as follows:

$$MAC(i, j) = \frac{Y_i \cdot Y_j}{|Y_i| \times |Y_j|}$$

where $Y_i$ and $Y_j$ denote the spectrum vectors of the $i^{th}$ portion and the $j^{th}$ portion in the bridge structure respectively, $Y_i \cdot Y_j$ denotes the inner product operation of the spectrum vectors, $|Y_i|$ and $|Y_j|$ denote the lengths of the vectors $Y_i$ and $Y_j$. Each element in the MAC coefficient matrix represents the degree of similarity between two spectrum vectors, wherein the elements in the diagonal must equal 1. The magnitude of the elements in the $i^{th}$ line or the $i^{th}$ column of the MAC coefficient matrix may reflect the damage condition corresponding to a certain spectrum vector $Y_i$, and thus is namely the damage index of the position corresponding to the spectrum vector $Y_i$.

The damage position determining apparatus determines a position of damage in the structure based on the damage index at each position of the surface of the to-be-detected bridge. For instance, the damage position determining apparatus may determine the position where the damage index abruptly drops as a position where a damage exists. This is because if the structure is not damaged, the graphical curve of the damage index should be relatively smooth; if the curve drops abruptly at some position, it means that a damage occurs at this position, and the greater amplitude the drop has, the more severe the damage is.

By means of the above serial steps of processing by the signal processing apparatus, the bridge damage information may be immediately obtained, such as a degree and a position of the damage, etc. For more detailed contents and principles of data detection and processing, they have already been disclosed in related prior art patents and will not be described here in detail.

Furthermore, the detection system of embodiments of the invention may be used without interrupting the bridge traffic and therefore requires arranging a signal separation module and a noise filtering module for processing the detection signal, so as to improve a signal-to-noise ratio of the signal and reach a desired signal detection result.

The above-said tap controlling apparatus 22 and signal processing apparatus 4 may be integrated into a computer system, which computer system may be further integrated into the driving apparatus 10.

In conjunction with FIG. 1 to FIG. 3, a simple application of the tap-scan bridge damage detection system of embodiments of the invention is described as follows. The mobile cart 1 is pulled by the driving apparatus 10 to move on the to-be-detected bridge, and the tap apparatus 21 mounted on the mobile cart 1 meanwhile applies a tap load to the cart body under the control of the tap controlling apparatus 22, where a frequency and a magnitude of the tap load should both be desirable. The tap load is finally applied to the to-be-detected bridge through transfer by the cart body and the wheels of the mobile cart, and anywhere on the surface of the bridge the cart travels past should undergo the tap-scan. Upon receiving the tap load the to-be-detected bridge makes a response and generates a response signal on e.g. acceleration, displacement, velocity and so on. Due to interaction between the bridge surface and the mobile cart, the response signal is also transferred by the cart and is finally acquired by the signal pickup apparatus 31 mounted on the cart, where the magnitude, etc. of a transient value of the response signal may reflect the structural feature of the to-be-detected bridge at the position of tap. In the present embodiment, the signal pickup apparatus is an acceleration sensor and accordingly, the response signal as acquired is an acceleration spectrum. The bridge response signal acquired by the signal pickup apparatus 31 is finally communicated to the signal processing apparatus 4, where corresponding signal filtering, signal conversion, data manipulation, data conversion, etc. are performed to finally output a processed result capable of reflecting the bridge damage information. Throughout the detection process of the detection system according to embodiments of the invention, detection signals may be obtained by the mobile cart scanning the to-be-detected bridge without requiring traffic blocking, where the operation is simple and easy to implement with high efficiency, and it yields high accuracy at a low cost, with accurate detection results obtainable without the necessity to interrupt bridge traffic and therefore the implementation strongly operable. By means of the tap-scan bridge damage detection system of embodiments of the invention, the damage status of a bridge may be readily learnt with convenience, so that potential risks at the bridge may be discovered in time, thus avoiding the occurrence of bridge accidents.

It should be noted that the above embodiments illustrate rather than limit the invention, and that those skilled in the art will be able to design alternatives without departing from the scope of the appended claims. In the claims, any reference signs placed between parentheses shall not be construed as limiting the claim. The word "comprise" does not exclude the existence of elements or steps other than those listed in a claim. The word "a" or "an" preceding an element does not exclude the existence of a plurality of such elements. Embodiments of the invention may be achieved by means of hardware comprising several different elements and by means of an appropriately programmed computer. In unit claims listing several means, several of these means may be embodied by one and the same item of hardware. The use of ordinal words such as first, second and third does not represent any order, but instead, they may be interpreted as naming.

Additionally, it should be noted that the language used in the present description is selected mainly for readability and teaching purposes, rather than for interpreting or limiting the subject matter of embodiments of the invention. Therefore, without deviating from the scope and spirit of the appended claims, many modifications and alterations are obvious to those ordinarily skilled in the art. For the scope of embodiments of the invention, the disclosure made herein for embodiments of the invention is not restrictive but illustrative, and the scope of embodiments of the invention is defined by the appended claims.

What is claimed is:

1. A tap-scan bridge damage detection system, comprising:
   a mobile cart capable of moving on a to-be-detected bridge;
   a tap subsystem mounted on the mobile cart for applying a tap load to the to-be-detected bridge, wherein the tap subsystem comprises a tap apparatus and a tap controlling apparatus, wherein the tap apparatus comprises a vibration shaker and the tap controlling apparatus comprises a controller for the vibration shaker;
   a signal acquisition subsystem mounted on the mobile cart for acquiring a response signal transferred from the to-be-detected bridge to the mobile cart, wherein the signal acquisition subsystem comprises a signal pickup apparatus, wherein the signal pickup apparatus comprises at least one of the following: an acceleration sensor, a velocity sensor, and a displacement sensor; and
   a signal processing apparatus connected to the signal acquisition subsystem for receiving, processing the signal acquired by the signal acquisition subsystem, and outputting the processed result of bridge damage information, said signal processing apparatus comprising a computer system configured to processing signals acquired by the signal acquisition subsystem.

2. The tap-scan bridge damage detection system according to claim 1, wherein the signal processing apparatus comprises:
   a spectrum obtaining apparatus connected to the signal pickup apparatus and used for transforming the signal detected by the signal pickup apparatus to obtain a signal spectrum at each position of the bridge surface;
   a spectrum envelope extracting apparatus used for extracting from the signal spectrum a spectrum envelope corresponding to a frequency band of the tap force from the tap apparatus;
   a damage index calculating apparatus for calculating a damage index at each position of the surface of the to-be-detected bridge according to the extracted spectrum envelope; and
   a damage position determining apparatus for determining a position of damage in the structure based on the damage index at each position of the surface of the to-be-detected bridge.

3. The tap-scan bridge damage detection system according to claim 1, wherein
   the tap apparatus is mounted on the mobile cart for generating the tap load and applying the tap load to the to-be-detected bridge; and
   the tap controlling apparatus is connected to the tap apparatus and used for controlling the tap apparatus to generate a predetermined tap load.

4. The tap-scan bridge damage detection system according to claim 1, further comprising a driving apparatus, the mobile cart being connected to the driving apparatus and driven by the driving apparatus to move on the to-be-detected bridge.

5. The tap-scan bridge damage detection system according to claim 1, wherein the mobile cart comprises:
   a cart body; and
   wheels mounted on the cart body, the wheels being rigid wheel disks and being in direct contact with the surface of the to-be-detected bridge.

6. The tap-scan bridge damage detection system according to claim 5, wherein the vibration shaker is mounted on the cart body of the mobile cart, wherein the vibration shaker produces a vibration excitation force that acts upon the cart body of the mobile cart, and the tap load is transferred to the to-be-detected bridge via the mobile cart.

7. The tap-scan bridge damage detection system according to claim 5, wherein the wheels comprise a front wheel and two rear wheels, the front wheel being located on a longitudinal axis of the cart body of the mobile cart, and the two rear wheels being mounted symmetrically at two sides of the longitudinal axis of the cart body.

8. The tap-scan bridge damage detection system according to claim 1, wherein the signal pickup apparatuses is mounted on the mobile cart for acquiring the response signal transferred from the to-be-detected bridge to the mobile cart.

9. The tap-scan bridge damage detection system according to claim 8, wherein the signal pickup apparatus comprises an acceleration sensor.

10. The tap-scan bridge damage detection system according to claim 9, wherein the acceleration sensor is one in number and is installed on the through-shaft of the two rear wheels of the mobile cart.

11. The tap-scan bridge damage detection system according to claim 10, wherein the acceleration sensor is located at the center of the through-shaft, and the tap apparatus is located directly above the acceleration sensor.

12. A tap-scan bridge damage detection system, comprising:
a mobile cart capable of moving on a to-be-detected bridge;
a tap subsystem mounted on the mobile cart for applying a tap load to the to-be-detected bridge;
a signal acquisition subsystem mounted on the mobile cart for acquiring a response signal transferred from the to-be-detected bridge to the mobile cart, wherein the signal acquisition subsystem comprises one or more signal pickup apparatuses which mounted on the mobile cart for acquiring the response signal transferred from the to-be-detected bridge to the mobile cart, wherein the one or more signal pickup apparatuses comprise at least one of the following: an acceleration sensor, a velocity sensor, and a displacement sensor; and
a signal processing apparatus connected to the signal acquisition subsystem for receiving, processing the signal acquired by the signal acquisition subsystem, and outputting the processed result of bridge damage information, said signal processing apparatus comprising a computer system configured to processing signals acquired by the signal acquisition subsystem;
a pulling vehicle for connecting to the mobile cart and driven by the pulling vehicle to move on the to-be-detected bridge;
the mobile cart comprises:
a rigid cart body, wherein each parts of the cart body are interconnected by rigid connection, and
wheels mounted on the cart body, the wheels being rigid wheel disks and being in direct contact with the surface of the to-be-detected bridge;
the tap subsystem comprises:
a tap apparatus mounted on the mobile cart for generating a tap load and applying the tap load to the to-be-detected bridge; and
a tap controlling apparatus connected to the tap apparatus for controlling the tap apparatus to generate a predetermined tap load;
wherein, the tap apparatus is a vibration shaker, and the vibration shaker is mounted at the center of the cart body of the mobile cart, wherein the signal pickup apparatus is one acceleration sensor which is installed at the center of the through-shaft of the two rear wheels of the mobile cart; and the vibration shaker is located directly above the acceleration sensor, such that a vibration excitation force produced by the vibration shaker acts upon the cart body of the mobile cart, and then the tap load is transferred to the to-be-detected bridge via the mobile cart.

13. The tap-scan bridge damage detection system according to claim 12, wherein the signal processing apparatus comprises:
a spectrum obtaining apparatus connected to the signal pickup apparatus and used for transforming the signal detected by the signal pickup apparatus to obtain a signal spectrum at each position of the bridge surface;
a spectrum envelope extracting apparatus used for extracting from the signal spectrum a spectrum envelope corresponding to a frequency band of the tap force from the tap apparatus;
a damage index calculating apparatus for calculating a damage index at each position of the surface of the to-be-detected bridge according to the extracted spectrum envelope; and
a damage position determining apparatus for determining a position of damage in the structure based on the damage index at each position of the surface of the to-be-detected bridge.

14. The tap-scan bridge damage detection system according to claim 12, wherein the wheels comprise a front wheel and two rear wheels, the front wheel being located on a longitudinal axis of the cart body of the mobile cart, and the two rear wheels being mounted symmetrically at two sides of the longitudinal axis of the cart body.

* * * * *